United States Patent [19]
Freiberg

[11] Patent Number: 5,139,494
[45] Date of Patent: Aug. 18, 1992

[54] MULTIWAVELENGTH MEDICAL LASER METHOD

[75] Inventor: Robert J. Freiberg, Mission Viejo, Calif.

[73] Assignee: Premier Laser Systems, Inc., Irvine, Calif.

[21] Appl. No.: 754,327

[22] Filed: Sep. 4, 1991

Related U.S. Application Data

[63] Continuation of Ser. No. 634,933, Dec. 27, 1990, abandoned, which is a continuation of Ser. No. 269,501, Nov. 10, 1988, abandoned.

[51] Int. Cl.$^5$ .............................................. A61N 5/06
[52] U.S. Cl. ........................................ 606/3; 606/10; 606/15; 606/16
[58] Field of Search .................... 606/3, 7–12, 606/15, 16; 128/395–398

[56] References Cited

U.S. PATENT DOCUMENTS

| | | | |
|---|---|---|---|
| 4,170,997 | 10/1979 | Pinnow et al. | 128/395 |
| 4,233,493 | 11/1980 | Nath | 128/398 X |
| 4,408,602 | 10/1983 | Nakajima | 128/303.1 |
| 4,503,854 | 3/1985 | Jako | 128/303.1 |
| 4,537,193 | 8/1985 | Tanner | 128/303.1 |
| 4,538,609 | 9/1985 | Takenaka et al. | 128/303.1 |
| 4,539,987 | 10/1985 | Nath et al. | 128/303.1 |
| 4,573,465 | 3/1986 | Sugiyama et al. | 128/303.1 |
| 4,592,353 | 6/1986 | Daikuzono | 128/303.1 |
| 4,641,912 | 2/1987 | Goldenberg | 128/303.1 |
| 4,693,244 | 9/1987 | Daikuzono | 128/303.1 |
| 4,791,927 | 12/1988 | Menger | 128/303.1 |
| 4,854,315 | 8/1989 | Stack et al. | 606/15 |

FOREIGN PATENT DOCUMENTS

| | | | |
|---|---|---|---|
| B38742 | 8/1985 | Australia . | |
| 0198959 | 10/1986 | European Pat. Off. | 128/303.1 |
| 0214712 | 3/1987 | European Pat. Off. . | |
| 2717421 | 11/1978 | Fed. Rep. of Germany | 128/303.1 |
| 2809007 | 9/1979 | Fed. Rep. of Germany | 128/303.1 |
| 3528531 | 2/1987 | Fed. Rep. of Germany | 128/303.1 |
| 8705794 | 10/1987 | World Int. Prop. O. | 128/303.1 |

OTHER PUBLICATIONS

Wolbarsht, Myron L., "Laser Surgery: CO2 or HF", IEEE Journal of Quantum Electronics, vol. QE-20, No. 12, Dec. 1984.

*Primary Examiner*—Lee S. Cohen
*Attorney, Agent, or Firm*—Knobbe, Martens, Olson & Bear

[57] ABSTRACT

A medical system for transmitting and delivering to a tissue site multiwavelength therapeutic radiant energy along a common optical pathway. Also included is a laser catheter suitable for engaging multiple sources of laser energy and transmitting multiwavelength therapeutic laser energy along a common optical path for delivery to a worksite.

10 Claims, 4 Drawing Sheets

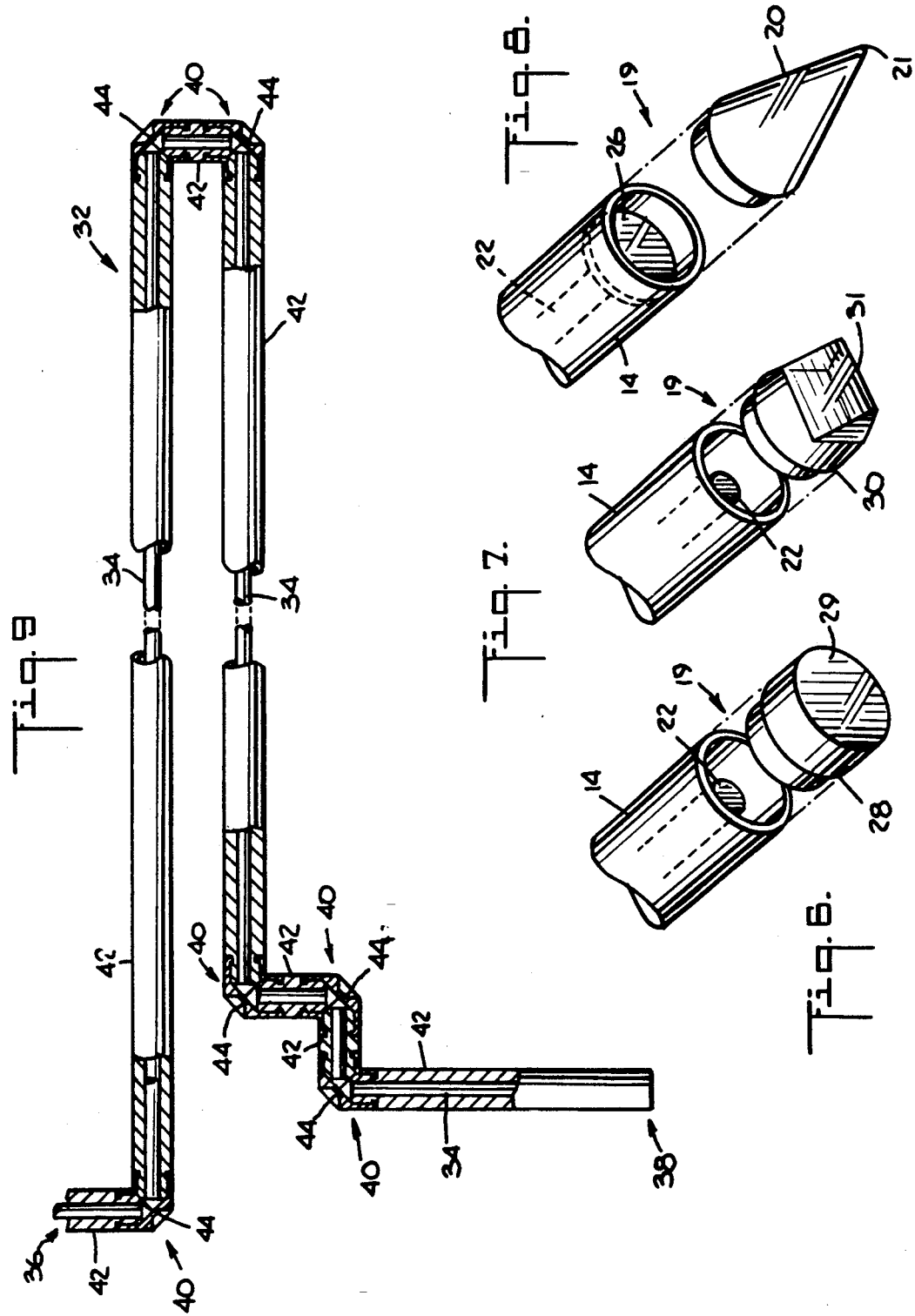

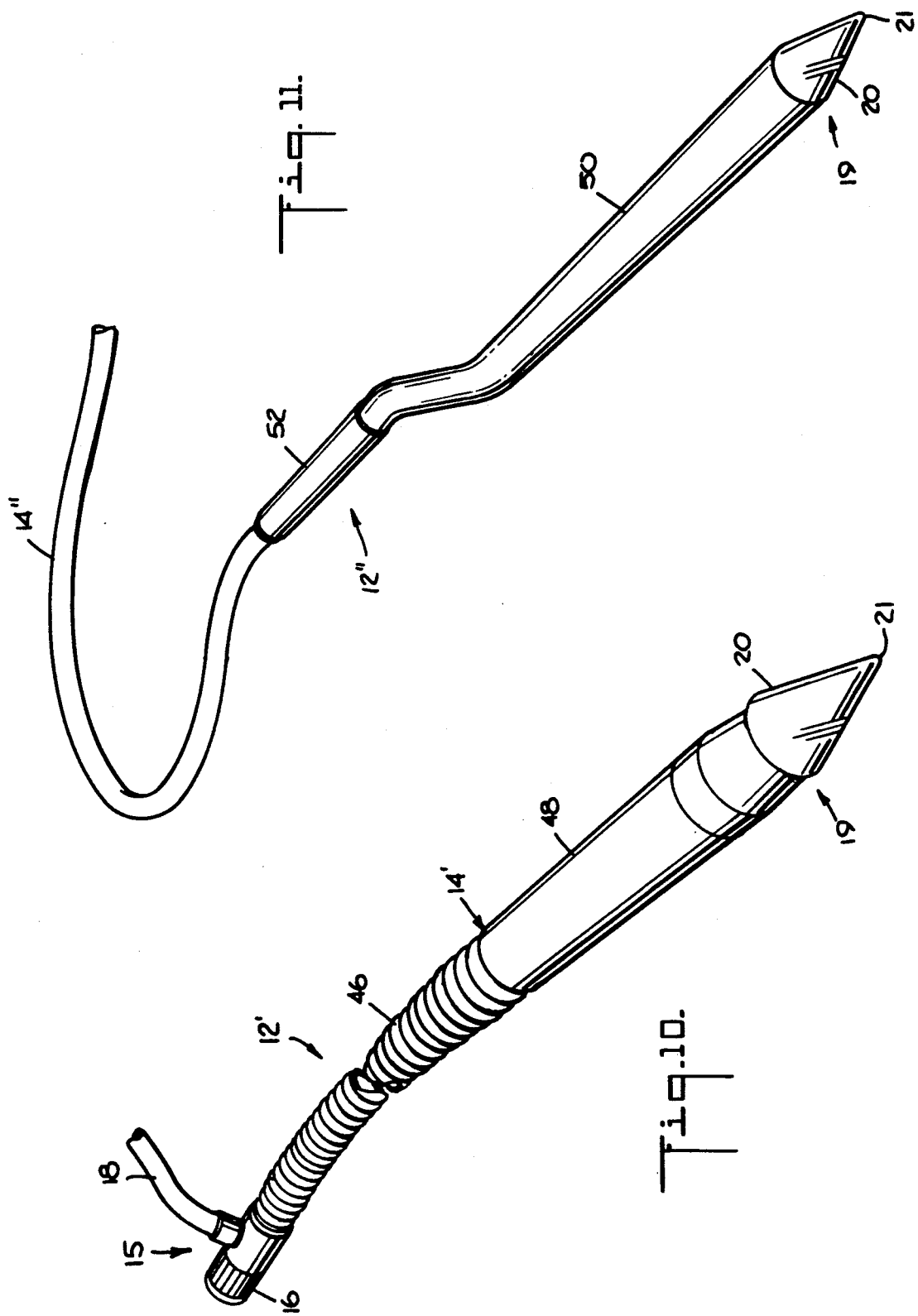

MULTIWAVELENGTH MEDICAL LASER METHOD this application is a continuation, of application Ser. No. 634,933, filed Dec. 27, 1990, now abandoned, which is a continuation of application Ser. No. 269,501, filed Nov. 10, 1988, now abandoned.

BACKGROUND OF THE INVENTION

The present invention pertains generally to medical laser systems and, more particularly, the invention relates to the transmission and delivery of therapeutic radiant energy from two or more energy sources to a tissue site with the transmission and delivery being conducted along a common optical pathway. The invention also includes a laser catheter having a single optical pathway capable of transmitting therealong multiple wavelength of therapeutic laser energy for delivery to a worksite.

Current laser surgery is limited by a physician's inability to tailor the dosimetry of a conventional laser to the particular clinical application of interest. One procedure, for example, such as a tonsillectomy, requires a degree of precise cutting but such a procedure is also vascular in nature and requires coagulation. Another procedure, as an example in the other extreme, is a completely avascular procedure, such as bone or meniscal surgery, which requires no coagulation. Presently, to accomplish cutting and coagulation through use of medical laser technology, a physician uses laser energy of different wavelengths delivered to the worksite along different pathways. Commonly, the physician will utilize independent laser sources and deliver the laser energy along two or more optical paths as, for example, through use of a plurality of catheters, articulated arms or hollow waveguides.

Clearly, there exists a need for a surgical tool, such as an electrocautery unit, which provides the physician with a simple, accurate means to precisely select the right combination of laser dosimetries to be able to adjust the coagulating and cutting capability of the laser for energy delivery to a tissue site through a single delivery system. Accordingly, I have invented a medical system which uses multiple wavelengths of therapeutic radiant energy for delivery along a common optical path to allow a physician to precisely incise, vaporize, anastomose and coagulate both hard and soft tissues during surgery through the use of a single delivery system.

SUMMARY OF THE INVENTION

The present invention is directed toward a medical system for transmitting energy to a tissue site comprising at least two sources of therapeutic radiant energy and means defining a common optical path for delivering therealong the energy to the tissue site. The optical path may be a catheter, one or more optical fibers, a hollow waveguide or an articulated arm. Additionally, the optical path may be a combination of one or more optical fibers and a hollow waveguide or one or more optical fibers and an articulated arm. Also, the articulated arm might include a hollow waveguide, reflective optics or transmission optics.

The therapeutic energy sources are lasers, particularly, tissue cutting, tissue ablating, tissue coagulating and tissue anastomosing lasers. Laser energy may be separately, simultaneously or alternately delivered from the sources to the tissue site. A visible aiming beam may also be delivered along the optical path to direct the energy to the desired tissue site location. The cutting and ablating lasers have wavelengths in the ranges of from about 0.1 to about 0.3 microns and from about 2.0 to about 12.0 microns. One preferred range in the higher range might be from about 2.7 to about 3.3 microns and another from about 5.5 to about 12.0 microns. An Excimer laser may be used to generate about an 0.2 micron wavelength in the lowest range. An Erbium laser might be used to generate about a 2.9 micron wavelength and a Carbon Dioxide laser might be used to generate about a 10.6 micron wavelength. A Holmium laser might be used to generate about a 2.1 micron wavelength. The coagulating and anastomosing lasers have wavelengths in the range of from about 0.3 to about 2.0 microns, with a Neodymium laser preferably being used to generate either about a 1.06 or about a 1.32 micron wavelength. Alternatively, a wavelength in the 0.3 to 2.0 micron range may be between about 0.4 to about 0.7 microns, preferably being generated by a tunable dye laser or a metal vapor laser.

The optical fiber may be chalcogenide, sapphire, heavy metal fluoride, halide crystal, silica or non-oxide glasses. Preferably, the fiber is either zirconium fluoride or silica based fiber. The fiber outside diameter might range from about 85 to about 600 microns with a preferred fiber diameter range being from about 180 to about 250 microns.

The invention further embodies a medical system comprising two or more sources of therapeutic laser energy and a catheter at a first end coupled to the energy sources, with the catheter having a body housing at least one elongate optical fiber defining a common pathway for delivering therealong the energy to a second end of the catheter.

The invention additionally embodies a medical instrument comprising a laser catheter at a first end adapted to be connected to two or more sources of therapeutic laser energy, with the catheter having a body portion defining a common pathway for delivering therealong the energy to a second end of the catheter. The catheter body includes at least one optical fiber, preferably a single optical fiber. The fiber may be a solid core fiber. The catheter body portion might further include a hollow flexible waveguide. Preferably, the energy sources operate at different output wavelengths. In one form, the catheter body portion includes a handpiece and a reinforced outer casing, while in another form, the catheter body portion proximate to the second end further includes a handpiece and a semirigid housing.

In a preferred form, the medical instrument comprises a flexible catheter adapted to be held by hand, and near the second end, the catheter further includes means for focusing the energy delivered to the second end. Focusing might be by means of a low optical loss high heat capacity contact tip ending in a point, a curved surface or an edge. Preferably, the tip is a sapphire tip. Alternatively, focusing may be by means of either a low optical loss high heat capacity plano convex lens or a low optical loss high heat capacity spherical lens. In addition to these last two named focusing means, the end of the catheter might further include a contact tip having an end configuration assuming a point, a curved surface or an edge. Lastly, the second end of the catheter might include a low optical loss high heat capacity window alone or in combination with a contact tip ending in a point, a curved surface, an edge or a flat surface.

BRIEF DESCRIPTION OF THE DRAWINGS

FIGS. 6 and 7 show additional modifications of the end portion of the catheter, with FIG. 6 providing a flat end and FIG. 7 providing an end tapered to an edge.

FIG. 8 shows yet another catheter end portion modification wherein the window of FIG. 5 and the tip of FIG. 3 are embodied in the same instrument.

FIG. 9 schematically illustrates an articulated arm having a hollow waveguide included therein.

FIG. 10 depicts an external use laser energy delivery probe.

FIG. 11 illustrates a semirigid, laser delivery, endoscopic probe.

DETAILED DESCRIPTION OF THE PREFERRED EMBODIMENTS

Figure 1:
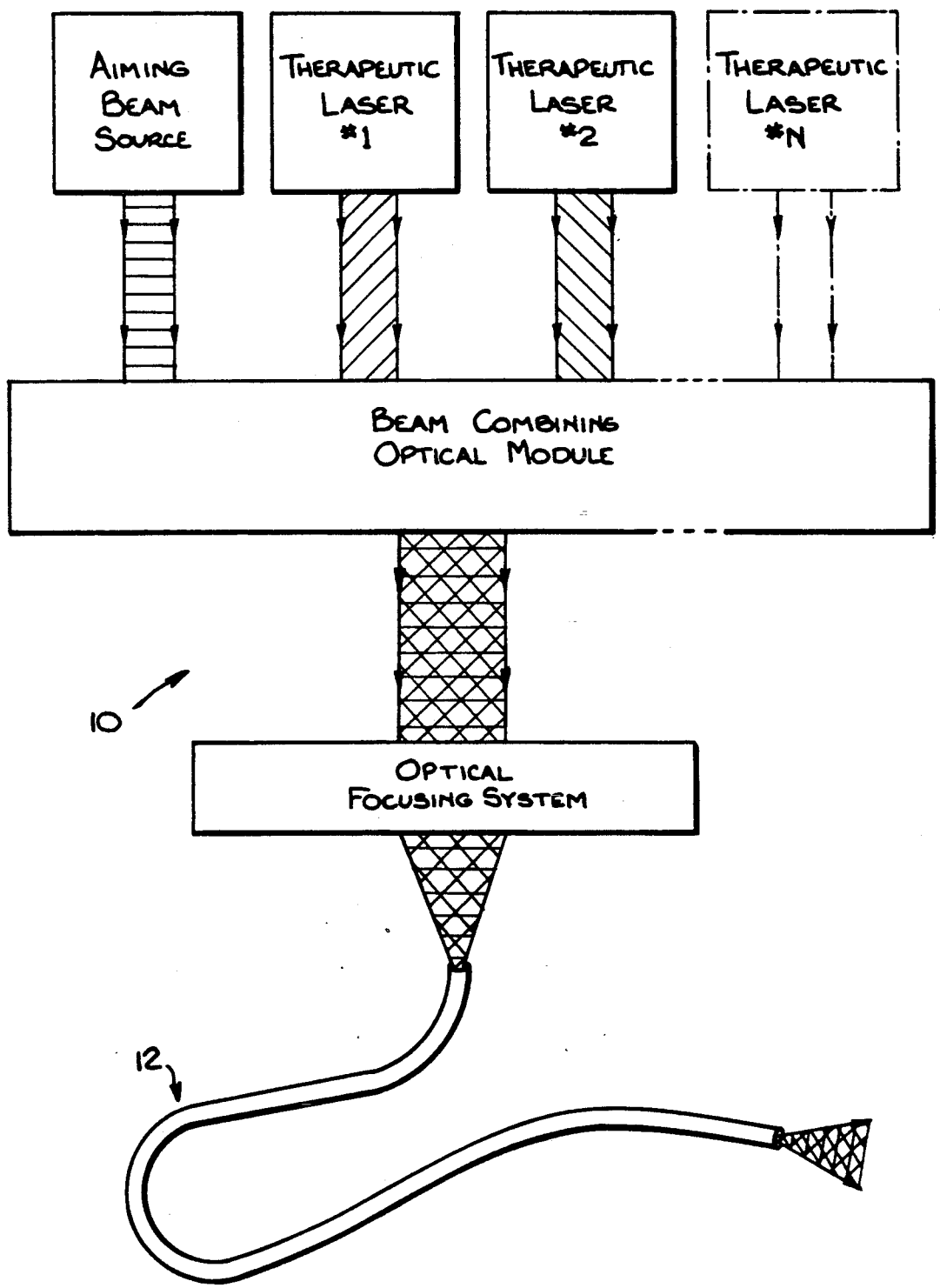
FIG. 1 is a schematic representation of a multiwavelength medical laser system embodying the principles of the present invention.

The description herein presented refers to the accompanying drawings in which like reference numerals refer to like parts throughout the several views. Referring to FIG. 1, in accordance with the priciples of the present invention, there is illustrated a schematic representation of a multiwavelength medical laser system 10. The system includes at least two therapeutic laser sources #1 and #2 and an aiming beam. Additional therapeutic laser sources may be added as desired. Energy from the sources are conveyed to a beam combining optical module for subsequent conveyance to an optical focusing system. Energy from the optical focusing system is then transmitted to a flexible catheter 12, adapted to be held by hand, for delivery therethrough to a tissue site (not shown). Specific detail is not provided with respect to beam combining and focusing for such is within the purview of one skilled in the art.

Figure 2:
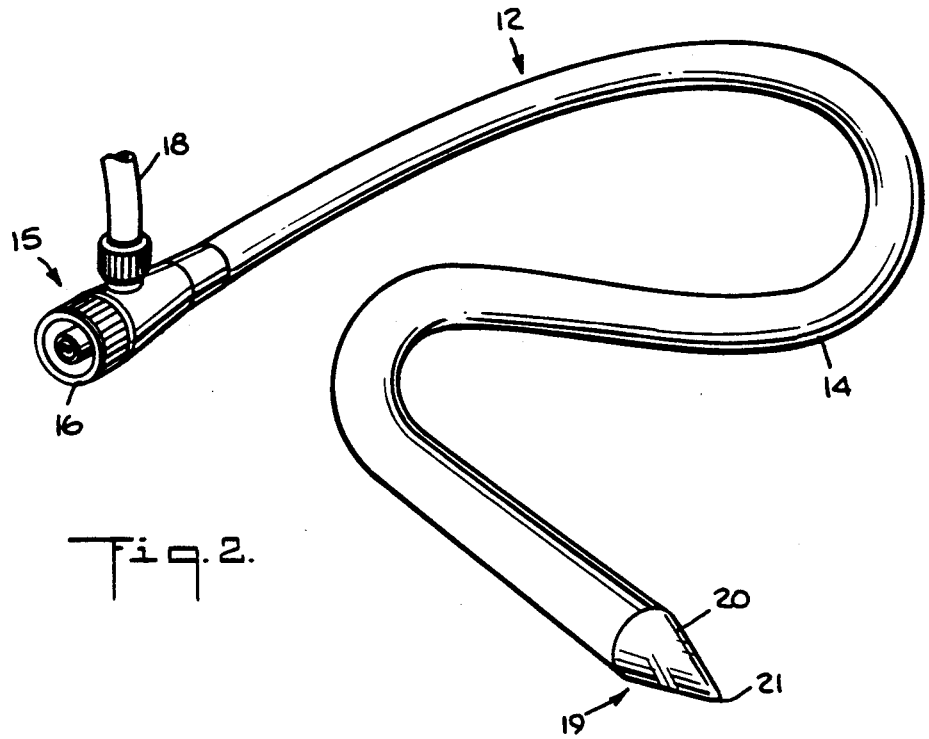
FIG. 2 is a schematic representation of a flexible laser catheter like that shown in FIG. 1 but illustrating modified end portions.

Turning to FIG. 2, there is shown catheter 12 in greater detail. The catheter has a body portion 14 and, at proximal end 15 of the catheter, there is a connector 16 for coupling the catheter to the optical focusing system and energy sources of FIG. 1. Also shown is a gas flow delivery system 18 and, at distal end 19 of the catheter, there is illustrated a low optical loss high heat capacity conical tissue contact tip 20 ending in a tissue engaging point 21. Connector 16 is a conventional coupling means and gas flow delivery, from a source not shown, is provided for cooling purposes at the distal end of the fiber (at end 19) and particularly at the catheter tip.

Figure 3:
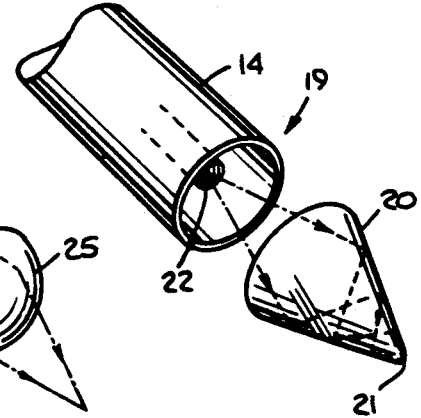
FIG. 3 is an enlarged partial view of the catheter of FIG. 2 showing an exploded view of the end portion and including an optical fiber and showing the focusing of the radiant energy delivered to and exiting from the catheter tip.

FIG. 3 is an enlarged partial view of catheter 12 illustrating an exploded view of end 19. An optical fiber 22 is shown located in body portion 14. Although the details are not shown, optical fiber 22 traverses the length of catheter 12 and is secured at both ends of the catheter but the fiber is flexible and freely movable between the fixed ends. Tip 20 is shown by the arrows as focusing the energy delivered to the end of the tip so that focused energy exits the tip at the distal end or point 21. It is the end of tip 20 which, in use, contacts the tissue site.

Figure 5:
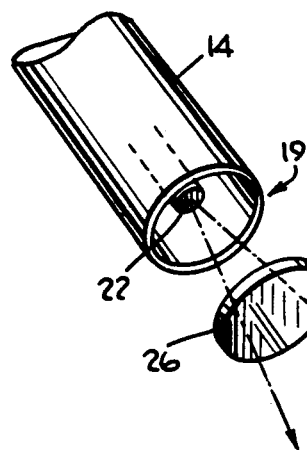
FIGS. 4 and 5 show modified embodiments of the end portion of the catheter as shown in FIG. 3 including an optical fiber and showing the focusing of radiant energy, by means of a lens (FIG. 4), and the divergence of radiant energy, by means of a window (FIG. 5), exiting the catheter tip.
Figure 4:
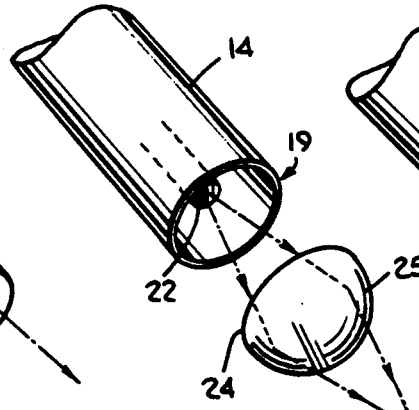

FIGS. 4-8 show detail much like that illustrated in FIG. 3 but with slightly different end configuration. Specifically, in FIG. 4, low optical loss high heat capacity plano convex focusing lens 24 having curved surface 25 is shown instead of conical tip 20. Lens 24 focuses the delivered energy beyond the lens as shown by the arrows. Therefore, in use, lens 24 customarily will not come into contact with the tissue being treated. It is the focused energy at the focal point which will make tissue contact. Instead of plano convex lens 24, a spherical lens (not shown) could have been used and its function would be like that of lens 24. In FIG. 5, low optical loss high heat capacity window 26 is illustrated. In the end embodiment of FIG. 5, as can be seen by the arrows, the radiant energy is not focused but is instead divergent which allows for a greater area of radiant energy to tissue contact. FIG. 6 illustrates a low optical loss high heat capacity tissue contact tip 28 having flat tissue contact surface 29. Although not shown by arrows, energy exits tip 28 following a path much like that shown for the energy path depicted in FIG. 5. FIG. 7 illustrates a low optical loss high heat capacity tissue contact tip 30 having tissue contact edge 31. Although not shown by arrows, energy is focused in tip 30 so that the energy exits the tip along the length of edge 31. FIG. 8 is much like the end configuration of FIG. 3 but further includes window 26. Focused energy is delivered to a tissue site in the same manner depicted in FIG. 3. It should be understood that, within the scope of the inventon, to provide a physician with a versatile instrument, a focusing contact tip could be used with a nonfocusing element. Like the FIG. 8 depiction, lens 24 and tips 28, 30 could be used in combination with window 24. Preferably, all tissue contact tips are made of sapphire but diamond tips could also be used. Also, preferably, the aforesaid high heat capacity elements specified are capable of withstanding heat in the 300° to 600° C. range.

Optical fiber 22 provides the common pathway along which therapeutic radiant energy is delivered. Preferably optical fiber 22 is a single, solid core fiber. However, it should be understood that a number of fibers could be used and that the fiber or fibers could be hollow core fibers. Additionally, the fiber could be used in conjunction with a hollow flexible waveguide or an articulated arm. A hollow flexible waveguide (discussed in greater detail in respect to FIG. 9) could be located within body portion 14 of catheter 12. Fiber construction could be of chalcogenide, sapphire, heavy metal fluoride, halide crystal, silica or non-oxide glasses, as desired. For many surgical applications, the fiber is preferably either zirconium fluoride or silica based fiber. Fiber size might range from about 85 to about 600 microns in outside diameter with a preferred fiber diameter range being from about 180 to about 250 microns.

Turning next to FIG. 9, in another embodiment, articulated arm 32, instead of catheter 12, is used for transmitting the radiant energy to the tissue site. In this view, arm 32 includes a hollow waveguide 34 disposed therein. End 36 is adapted to be connected to the optical focusing system and end 38 delivers the energy to the tissue site. Articulated arm 32 comprises a series of joints 40 separated by straight hollow portions 42 wherein at each joint 40 there is disposed one or more optical components 44 for delivering the radiant energy along the center axis of the straight segments. Optical components 44 may be reflective optics such as mirrors or transmission optics such as lenses or a combination of mirrors and lenses. Hollow waveguide 34 is a tube used to guide the energy waves delivered thereto for passage therethrough. While the articulated arm is shown to include waveguide 34, it should be understood that the invention also encompasses an articulated arm used without a waveguide. Additionally, it should be understood that a hollow waveguide, including internally disposed optical components 44, could be used without an articulated arm. As aforesaid, additionally encompassed within the scope of the invention is the use of optical fiber 22 in combination with either an articulated arm or a hollow waveguide, with the fiber being disposed inside the arm or waveguide. The fiber would traverse the length of the arm or waveguide and would replace optical components 44. End 38 could assume any of the configurations heretofore specified in respect to end 19 of catheter 12.

Turning lastly to FIGS. 10 and 11, there are shown alternate embodiments of laser energy delivery systems. Energy delivery probe 12' includes a body portion 14', a reinforced outer casing 46 and a handpiece 48. Endoscopic probe 12" includes a body portion 14", a semi-rigid housing 50 and a handpiece 52.

Therapeutic radiant energy from at least two sources is delivered along a common optical path to a tissue site. Preferably, the energy sources are laser energy sources which operate at different output wavelengths. The energy may either be infrared or visible but, preferably, infrared. Additionally, the aiming beam, which is visible radiant energy, is preferably transmitted along the same optical path and is used to precisely direct the therapeutic energy to the tissue site treatment location. Therapeutic energy from the different sources may be separately delivered to the tissue site, simultaneously delivered to the tissue site or alternately delivered to the tissue site. The energy sources may be two or more tissue cutting or tissue ablating lasers, two or more tissue coagulating or tissue anastomosing lasers, or the combination of one or more cutting or ablating laser and one or more coagulating or anastomosing laser.

Tissue cutting and tissue ablating lasers customarily operate in about 0.1 to about 0.3 and in about 2.0 to about 12.0 micron ranges. The tissue cutting and ablating lasers have wavelength ranges which correspond to strong energy absorption in the water vapor spectrum. Tissue coagulating and tissue anastomosing lasers customarily operate in a range of from about 0.3 to about 2.0 microns. The tissue coagulating and anastomosis lasers have wavelength ranges which correspond to weak energy absorption in the water vapor spectrum and simultaneously may correspond to strong energy absorption in the spectrum of some other tissue constituents such as hemoglobin and melanin.

A number of laser energy sources may be employed. An Excimer laser may be used to generate about a 0.2 micron wavelength as a cutting or ablating laser. An Erbium laser may be used to generate about a 2.9 micron wavelength cutting or ablating laser in a preferred range of from about 2.7 to about 3.3 microns. Alternatively, a Holmium laser may be used to generate about a 2.1 micron wavelength cutting or ablating laser in the preferred 2.0 to 12.0 range. A Carbon Dioxide laser may be used to generate about a 10.6 micron wavelength cutting or ablating laser in a preferred range of from about 5.5 to about 12.0 microns. A Neodymium laser may be used to generate either about a 1.06 micron wavelength or about a 1.32 micron wavelength coagulating or anastomosing laser. An alternate coagulating or anastomosing laser operating in a wavelength range of from about 0.4 to about 0.7 microns might be generated by a tunable dye laser or a metal vapor laser.

In a specific preferred embodiment of the invention shown in FIG. 1, the system incorporates two separate therapeutic laser energy sources, namely, Nd:Yag and Er:Yag lasers. The Er:Yag is a precise cutting tool at low repetition rates. Because the Er:Yag laser wavelength is at 2.9 microns, which coincides with the absorption band of water, the laser cuts both bone and soft tissue effectively. At higher repetition rates, it becomes more aggressive and can be utilized as an ablative tool for removing larger volumes of material. Energy per pulse and repetition rate can be precisely controlled completely independently of the Nd:Yag source. The Nd:Yag can produce a 1.06 micron, a 1.32 micron or a combination beam. At 1.06 micron, the laser is an extremely effective coagulator. On the other hand, it welds tissue effectively at 1.32 micron. This continuous wave Nd:Yag system also has a precisely controlled power level independent of the Er:Yag laser. The dosimetry parameters of each laser can be programmed independently, the output of each controlled concurrently through a single foot pedal, and the combined multiwavelength output delivered simultaneously through a common optical fiber delivery system.

Each of the two laser systems may be modular in nature and expandable to higher power levels. Each laser might consist of a resonator module, which incorporates the laser head, control electronics power meter and aiming beam, and a separate power module, which contains the power supply and cooling system. The laser head can be powered with a smaller power unit, such as 30W CW for the Nd system, or powered with a larger power unit, such as 60W CW.

The option exists for the laser energy from each laser to be delivered through its own fiber optic delivery system. For example the Nd:Yag laser energy may be delivered to the tissue through a first fiber while the Er:Yag may be focused through a second fiber. A preferred embodiment is to superimpose the Nd:Yag energy and the Er:Yag energy in a beam combining module as shown schematically in FIG. 1. The module colinearly aligns the Nd laser beam, the Er laser beam and the aiming beam simultaneously onto the tissue through a single fiber capable of transmitting visible, near infrared and mid-infrared wavelengths. The fiber preferably is either zirconium fluoride fiber or silica based fiber.

The fiber optic delivery system may be disposable or reusable. The preferred embodiment contains a zirconium fluoride fiber, a distal focusing lens, proximal connector and a catheter housing for sterility, hermeticity and structural integrity. Gas or fluid may pass through the catheter to cool the distal tip of the fiber and be directed on to the tissue as a means of preventing ablated tissue from splattering back on the distal lens of the catheter. A typical catheter for flexible endoscopic applications is shown in FIG. 2. FIG. 10 depicts a ruggedized, mechanical, reinforced probe for external laser surgical applications. FIG. 11 shows a probe integrated with a semi-rigid endoscopic introducer applicable for procedures in the field of ENT.

Using the present medical system, a physician may precisely cut using a pulsed 2.9 micron laser beam, may vaporize using either a 2.9 micron laser beam at a higher average power or a 1.06 micron beam, may coagulate with a 1.06 micron beam, weld with a 1.32 micron beam and guide therapeutic infrared laser radiation with a visible aiming beam. This laser radiation, which is generated by either separate lasers and/or combination lasers, may be delivered separately, simultaneously or alternately through a single fiber which can transmit from the visible through the mid-infrared range.

The present invention has been described herein with specific reference to the preferred embodiments thereof. However, those skilled in the art will understand that changes may be made in the form of the invention covered by the claims without departing from the scope and spirit thereof, and that certain features of the invention may sometimes be used to an advantage without corresponding use of the other features.

I claim:

1. A method comprising:
   using a first laser to generate a first beam of electromagnetic energy having a first wavelength on the order of 3 microns;
   using a second laser to generate a second beam of electromagnetic energy having a second wavelength on the order of 1 micron;
   coupling energy from said first laser to a metal halide optical fiber;
   coupling energy from said second laser to said metal halide optical fiber;
   guiding said energy having said first wavelength along said metal halide optical fiber at a dosage which cuts tissue;
   guiding said energy having said second wavelength along said metal halide optical fiber at a dosage which coagulates tissue;
   cutting tissue using said energy at said first wavelength; and
   coagulating tissue using said energy at said second wavelength.

2. The method of claim 1, wherein said metal halide fiber has a distal end, said method additionally comprising:
   cooling said distal end by transmitting a fluid along said metal halide optical fiber to said distal end.

3. The method of claim 2 wherein said fluid comprises a gas.

4. The method of claim 1, wherein said first wavelength is about 2.9 microns.

5. The method of claim 4, wherein said second wavelength is about 1.06 microns.

6. The method of claim 5, wherein the step of generating said second wavelength comprises the step of energizing a neodymium laser.

7. The method of claim 1, wherein said metal halide optical fiber comprises zirconium fluoride.

8. The method of claim 1, wherein the step of generating said first wavelength comprises the step of energizing an HF laser that produces a wavelength of about 2.9 microns.

9. The method of claim 1, wherein said guiding steps are performed simultaneously and said cutting and coagulating steps are performed simultaneously.

10. The method of claim 1, wherein the step of cutting tissue comprises cutting bone.

* * * * *